US009308388B2

(12) United States Patent
Chau

(10) Patent No.: US 9,308,388 B2
(45) Date of Patent: Apr. 12, 2016

(54) CERAMIC FOOTBATH BOOTS

(75) Inventor: Yiu Wing Chau, Hong Kong (HK)

(73) Assignee: GOLD OCEAN ASIA LIMITED, Hong Kong (HK)

( * ) Notice: Subject to any disclaimer, the term of this patent is extended or adjusted under 35 U.S.C. 154(b) by 733 days.

(21) Appl. No.: 13/696,080

(22) PCT Filed: May 10, 2011

(86) PCT No.: PCT/CN2011/073863
§ 371 (c)(1),
(2), (4) Date: Nov. 26, 2012

(87) PCT Pub. No.: WO2011/140967
PCT Pub. Date: Nov. 17, 2011

(65) Prior Publication Data
US 2013/0211296 A1    Aug. 15, 2013

(30) Foreign Application Priority Data

May 11, 2010 (CN) .......................... 2010 1 0168254

(51) Int. Cl.
A61H 35/00 (2006.01)
A61H 33/00 (2006.01)
(Continued)

(52) U.S. Cl.
CPC ................ *A61N 5/0613* (2013.01); *A43B 1/00* (2013.01); *A61H 35/006* (2013.01); *A47K 7/026* (2013.01);
(Continued)

(58) Field of Classification Search
CPC . A61H 35/006; A61H 33/00; A61H 33/0095; A61H 33/6005; A61H 33/6089; A61H 2205/12; A47K 7/026; A47K 3/022; A61N 5/0613; A61N 2005/0668; A43B 1/00; A43B 1/0009; A43B 7/12
See application file for complete search history.

(56) References Cited

U.S. PATENT DOCUMENTS 2,565,751 A * 8/1951 Birkle ........................... 604/293
3,003,261 A * 10/1961 Graham et al. ................. 36/2 R
(Continued)

FOREIGN PATENT DOCUMENTS

CN    2260607 Y    8/1997
CN    2318838 Y    5/1999
(Continued)

OTHER PUBLICATIONS

Machine Translation of KR 20070011868A, Jang, published Jan. 25, 2007.*
(Continued)

*Primary Examiner* — Valerie L Woodward
(74) *Attorney, Agent, or Firm* — Ella Cheong Hong Kong; Sam T. Yip

(57) ABSTRACT

Ceramic footbath boots, ceramic materials for manufacturing the ceramic footbath boots and application of the ceramic materials to the manufacture of the ceramic footbath boots are disclosed herein. The ceramic footbath boots include a pair of boot-like footbath containers (1). The footbath containers (1) are made of the ceramic materials, and the internal walls of the footbath containers are provided with net-like lines and papillary groups (2) corresponding to the reflex point zone of feet. The ceramic materials can: emit far infrared rays with wave length of 4-14 microns and the emitting rate of more than 0.92 at normal temperature; release negative ions automatically and permanently; continuously produce weak static current matching the bioelectric current of human bodies; and release mineral matters and trace elements needed by human bodies into water. The ceramic materials are preferably tourmaline-containing silicates.

11 Claims, 4 Drawing Sheets

(51) Int. Cl.
*A61N 5/06* (2006.01)
*A43B 1/00* (2006.01)
*A47K 7/02* (2006.01)

(52) U.S. Cl.
CPC ............. *A61H 33/00* (2013.01); *A61H 33/6005* (2013.01); *A61H 33/6089* (2013.01); *A61H 2201/0207* (2013.01); *A61H 2201/165* (2013.01); *A61H 2205/125* (2013.01)

(56) References Cited

U.S. PATENT DOCUMENTS

| | | | | |
|---|---|---|---|---|
| 3,026,540 | A * | 3/1962 | Barker | 4/622 |
| 3,283,756 | A * | 11/1966 | Turley | 601/166 |
| 3,478,738 | A * | 11/1969 | Cox et al. | 601/166 |
| 4,125,491 | A * | 11/1978 | Gorman | 524/476 |
| 4,497,313 | A * | 2/1985 | Kurosawa | 601/16 |
| 5,044,357 | A * | 9/1991 | Johns | 601/166 |
| 5,758,370 | A * | 6/1998 | Schwartz | 4/622 |
| 6,602,212 | B1 * | 8/2003 | Ahn | 601/154 |
| 7,096,918 | B2 * | 8/2006 | Lin | 160/171 |
| 7,328,476 | B1 * | 2/2008 | Heidemeyer, Jr. | 15/104.92 |
| 7,426,757 | B2 * | 9/2008 | Lev et al. | 4/622 |
| 2005/0015874 | A1 * | 1/2005 | Watanabe et al. | 4/622 |
| 2009/0181844 | A1 * | 7/2009 | Hashimoto | 501/135 |
| 2010/0229884 | A1 * | 9/2010 | Alony | 132/73.5 |
| 2010/0312201 | A1 * | 12/2010 | Hoege | 604/293 |

FOREIGN PATENT DOCUMENTS

| | | |
|---|---|---|
| CN | 2379125 Y | 5/2000 |
| CN | 1954747 A | 5/2007 |
| CN | 101100906 A | 1/2008 |
| CN | 201097673 Y | 8/2008 |
| KR | 10-2007-0011868 A | 1/2007 |

OTHER PUBLICATIONS

Machine Translation of CN 1954747A, Li, published May 2, 2007.*
Machine Translation of CN 2379125Y, Piao, published May 24, 2000.*
Machine Translation of CN 2318838Y, Ma, published May 19, 1999.*

* cited by examiner

CERAMIC FOOTBATH BOOTS

CROSS-REFERENCE TO RELATED APPLICATION

This is a national phase application of an International patent application number PCT/CN2011/073863 filed May 10, 2011, which claims priority from a Chinese patent application number 201010168254.6 filed May 10, 2010 that is now granted under the patent publication number CN101836776B, and the disclosure of which are incorporated herein by reference.

TECHNICAL FIELD

The present invention relates to a type of footbath product, particularly footbath boots made of ceramic materials including a formula, for example, the footbath boots are made of silicate-based ceramic material that contains tourmaline.

BACKGROUND ART

Footbath has a long history in China, and in practice, it has been evidently confirmed that it is very good for the human body and has become a regimen of the Chinese nation. At present, there are a wide variety of footbath products on the market, but traditional footbath and immersion containers thereof only allow both of users' legs to be placed flat in the same immersion space, and these containers mainly include wooden basins, wooden barrels and plastic basins. wooden basins, wooden barrels and plastic basins have many disadvantages, such as rapid cooling, low water level for immersion and both legs must be placed flat together while little or no free movement is allowed. In the Chinese patent application number 200510118945.4 and U.S. Pat. No. 4,497,313, a basin-shaped structure is disclosed. Moreover, in the U.S. Pat. No. 4,497,313, the footbath device disclosed therein is heated electrically. All the electrically-heated footbath devices need a power source and electric wires, as well as a draining outlet. Therefore, risks like electrical leakage and tripping due to electric wires, and shortcomings like incomplete drainage and inconvenient to clean, exist in these conventional products or technology.

In addition, some conventional footbath products also include a shoe-shaped structure, for example, those disclosed in the Chinese utility model patent application numbers 200720097195.1 and 95229747.7, which do not use electric heating, but these footbath products are complex in structure and inconvenient to use.

Moreover, some studies by Japan Far Infrared Rays Association (JIRA) have shown that ceramic materials can emit far infrared rays which may benefit human health more than bathing in hot water alone. Human body waste is normally excreted through sweat and urine in order to reinstate the homeostasis of the body. A wide variety of baths have been suggested in these studies to facilitate sweating. A particular type of ceramic material which can emit the most suitable wavelength of the far infrared rays and an optimal design of the footbath for our human body are two main focuses of the future development in this field.

Ibusuki Onsen hot spring in Kagoshima Prefecture is a famous sand bath in Japan, there is also a very prestigious rock bath—Tamagawa hot spring in Yamagata Prefecture. Both sand bath and rock bath exploit the heat energy emitted by heated silicate-based minerals, therefore the energy form is completely different from that of ordinary water baths, and the associated health benefits on human are also different. An artificial sand bath generally uses soy bean sized ceramic beads. The discrepancies between artificial sand baths and ordinary water baths can be investigated through comparison testing. FIG. 6 is spectrophotometric infrared radiation curves for ceramic beads bath and ordinary warm water bath. Curve 1 represents the ceramic bead sand bath and Curve 2 represents the ordinary water bath. FIG. 7 is a heat absorption curve of skin. From the two figures, capacity of ceramic beads and warm water to transfer heat to human body can be analyzed. The ordinary warm water bath provides great water energy to the human body, but little energy is delivered to the body muscle and other tissues, whereas ceramic beads bring beneficial effects to body tissues, indicating that different heat transfer characteristics result in different excretion effects on human body. Bathing in a sand bath at the temperature of 50 degrees for about 15 minutes induces heavy sweating, and leads to a weight loss of 800 g. It is known that sand bath promotes blood circulation and probably excretion of body waste and cholesterol through sweating.

Trace amount of radium is found in minerals close to hot springs, so the surrounding air contains radon. Air having negative ions which can benefit human health along with infrared rays emitted by hot rock produce double remedial effect. As ceramic far infrared ray emitters can be readily manufactured, the use of said emitters in artificial sand baths and rock baths and other areas is possible, and specifically such emitters would be an excellent material for health remedial purposes in the future.

The present invention provides footbath boots made of ceramic materials including but not limited to a formula, for example, tourmaline-containing and silicate-based ceramic footbath boots to overcome the shortcomings of the existing technologies.

SUMMARY OF THE INVENTION

The technical problem to be solved by the present invention is to provide ceramic footbath boot that overcome the shortcomings in the conventional products such as limited application, inconvenience and complex structure.

The present invention solves the technical problems in the conventional products by the following ways: a ceramic footbath apparatus includes a pair of boot-like footbath containers, characterized in that said footbath containers are made of ceramic materials including but not limited to a formula, for example, a silicate-based ceramic material that contains tourmaline. The footbath containers are sintered into a double-layered structure having a hollow space between the two layers, where the inner layer of the footbath containers has a plurality of honeycomb-shaped, hexagonal cylinder-shaped, or porous network-like lines; and are attached with a plurality of papillary extrusions corresponding to the reflex points of the feet.

The ceramic footbath boots according to the present invention, characterized in that the top open end of each of the footbath containers is configured to have a relatively more elevated front portion and a relatively lower rear portion. The relatively more elevated front portion of the open end of each boot further forms an arch shape for fixing a movable canopy and for users to hold the boot when pouring water therein or therefrom; the relatively lower rear portion has a U-shaped notch for ease of pouring water in or out of each of the boots.

The ceramic footbath boots according to the present invention, characterized in that each of the footbath containers further includes the movable canopy which is sewn with thermal insulating fiber and is provided at the top open end of each footbath container.

The ceramic footbath boots according to the present invention, characterized in that the canopy also has a zipper, drawstring or hook-and-loop fastener for adjusting tightness.

The ceramic footbath boots according to the present invention, characterized in that the inner layer of the footbath containers are marked with at least minimum and maximum water level lines.

The ceramic footbath boots according to the present invention, characterized in that the footbath containers are sintered into a double-layered structure with a hollow space between the two layers for heat retention and thermal insulation.

The ceramic footbath boots according to the present invention, characterized in that the inner layer of the footbath containers is non-glazed, so that the emission rate of far infrared rays is not weakened; the outer layer of the footbath containers is glazed to enhance heat retention and thermal insulation.

The present invention is structurally simple, easy for use and comfortable while providing excellent remedial health effects.

Figure Labels: 1. Foot container; 1.1. Inner layer of footbath container; 1.2. Outer layer of footbath container; 2. Papillary extrusions; 3. U-shaped notch; 4. Canopy; 5. Zipper/drawstring/hook-and-look fastener.

DETAILED DESCRIPTION OF THE PRESENT INVENTION

In the following, the present invention will be further described with reference to the accompanying drawings.

1. Structure of Ceramic Footbath Boots

Figure 1:
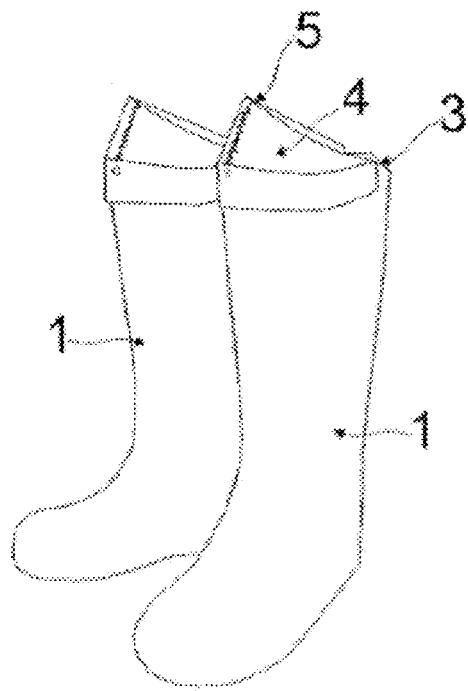
FIG. 1 is a schematic diagram of an explanatory example of the present invention.
Figure 2:
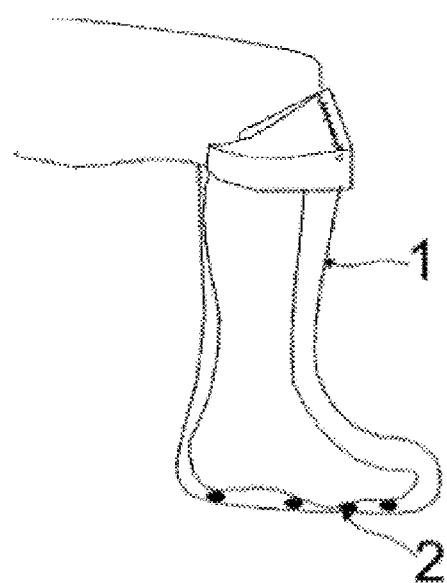
FIG. 2 is a diagram of the present invention in use.
Figure 3:
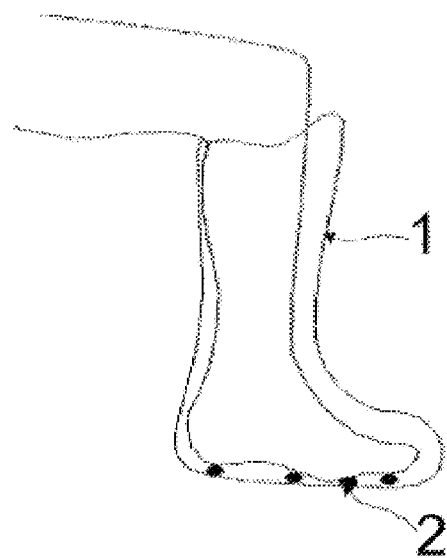
FIG. 3 is a schematic diagram of FIG. 2 without a canopy.
Figure 4:
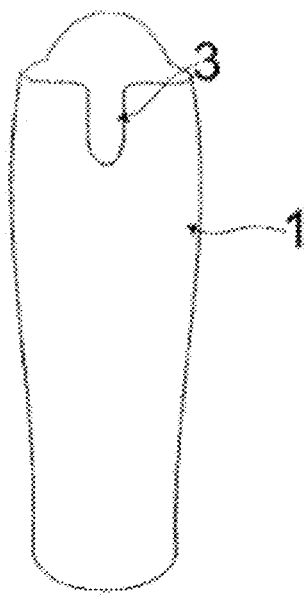
FIG. 4 is a rear view of the boot of the present invention.
Figure 5:
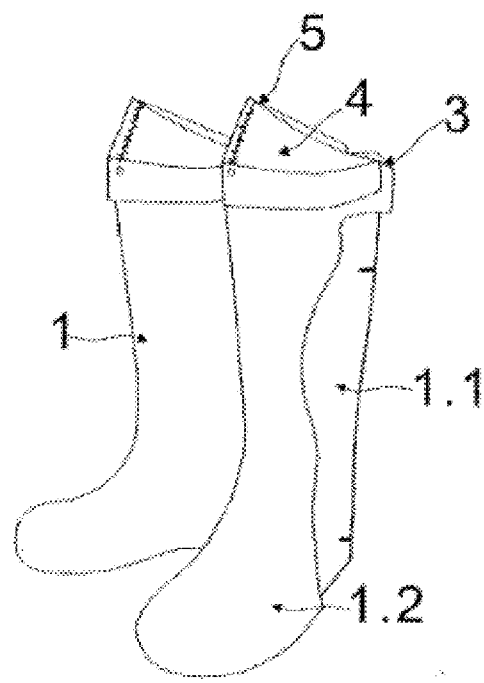
FIG. 5 is a schematic diagram illustrating the water level lines depicted in the present invention.
Figure 6:
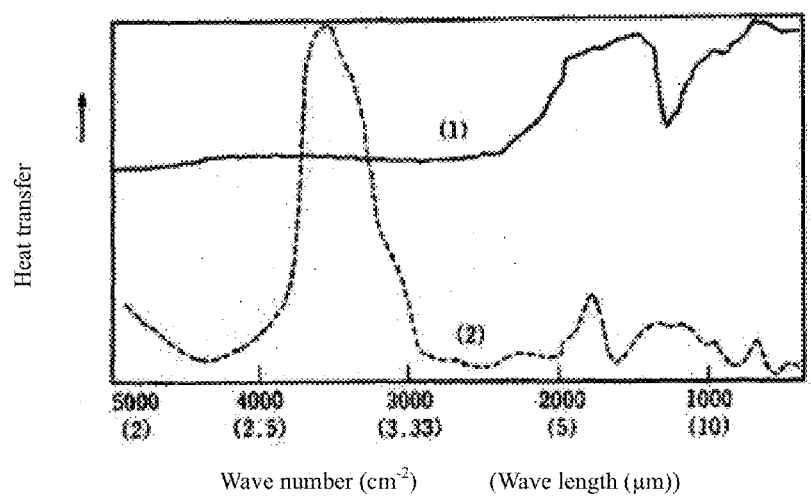
FIG. 6 is the spectrophotometric curves of the infrared radiation generated by the conventional ceramic sand beads and warm water in ordinary bath.
Figure 7:
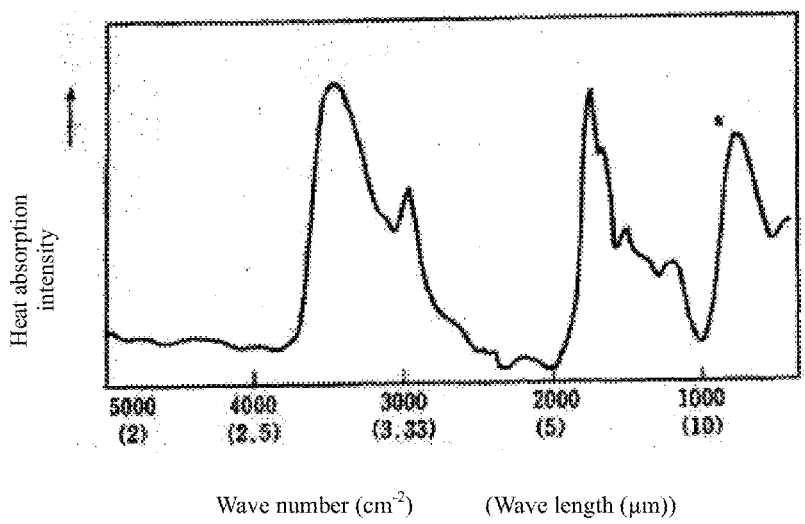
FIG. 7 is the heat absorption curve of the skin.

As shown in FIG. 1, ceramic footbath boots made of ceramic materials including but not limited to a formula are provided, for example, the silicate-based ceramic footbath boot that contains tourmaline, wherein each foot corresponds to each footbath boot, thus both legs need not be placed in the same footbath container as required by the conventional foot reflexology. The present invention comprises a pair of boot-like footbath containers (1), wherein said footbath containers (1) are made of ceramic materials including but not limited to a formula, for example, a silicate-based and tourmaline-containing ceramic material; the footbath containers (1) are sintered into a double-layered structure with a hollow space between the inner and outer layers (1.1, 1.2 in FIG. 5) to strengthen heat retention and thermal insulation; the inner layer 1.1 comprises a plurality of honeycomb-shaped, hexagonal cylinder-shaped or porous network-like lines; the surface of the inner layer 1.1 further comprises a plurality of papillary extrusions (2) corresponding to reflex point of the user's feet, a movable canopy (4) sewn with thermal insulating fiber is provided at the top open end of the footbath containers (1), as shown in FIG. 2. As shown in FIG. 3, the top open end of the footbath containers (1) has a relatively more elevated front portion and a relatively lower rear portion. The relatively more elevated front portion of the open end of the boot forms an arch shape for fixing the movable canopy (4) and for the user to hold the boot when pouring water therein or therefrom; the relatively lower rear portion has a U-shaped notch (3) for ease of pouring water in or out of the boot, as shown in FIG. 4. In addition, the movable canopy (4) also has a zipper, drawstring or hook-and-look fastener (5) to adjust tightness of the boots such that the open end can be tightened to prevent leaking of the hot water vapor from the inside of the ceramic footbath boots and to slow down the cooling rate of the hot water in the ceramic footbath boots. The movable canopy (4) is also detachable from the boot. The inner layer (1.1) of the footbath containers (1) also has at least minimum and maximum water level lines, as shown in FIG. 5. The inner layer (1.1) of the footbath containers is non-glazed so that the emission rate of far infrared rays is not weakened; the outer layer (1.2) of the footbath containers (1) are glazed to enhance heat retention and thermal insulation.

2. Ceramic Materials

The ceramic footbath boots of the present invention are made of ceramic materials including but not limited to a formula, for example, a silicate-based and tourmaline-containing ceramic material. The ceramic material of the present invention should have the following characteristics: 1. Ability to emit far infrared rays with a wavelength of 4-14 μm and at an emission rate of more than 0.92 at room temperature; 2. Ability to release negative ions automatically and permanently; 3. Ability to continuously produce weak static current [0.06 mA] that matches bioelectric current of the human body; 4. Ability to release at least 11 types of minerals and trace elements into water, including magnesium, sodium, iron, manganese, lithium, aluminum, boron, silicon, fluorine, hydrogen and oxygen, among which magnesium, iron, manganese, silicon, fluorine and boron are essential for or have significant physiological effects on the human body; 5. high applicability, the material can be fabricated into different structures accommodated to human body and is strong enough upon formation while it has outstanding features of thermal insulation and resistances to acid, alkali, corrosion and high temperatures. Furthermore, the inner layer of the footbath containers (1) includes a plurality of honeycomb-shaped, hexagonal cylinder-shaped or porous network-like lines. The inner layer also includes a plurality of papillary extrusions corresponding to reflex points of the feet. The ceramic footbath boots of the present invention is an ideal massage device to stimulate the reflex point zone of the feet after the boots are heated. As the ceramic footbath boots do not need a power source, it is energy-efficient, economical and durable. The present invention is also easy to use and clean, and environmental-friendly when being disposed.

Far infrared ray is a type of invisible light that lies between near-infrared rays and microwaves with a wavelength of about 4-1000 μm. It is an electromagnetic wave with a larger wavelength value of sunlight, and possesses perpendicular incidence, refraction, reflection and penetrability characteristics of light. The strong radiating capacity of ceramic material can heat up targeted objects directly without increasing the temperature of the surrounding air or objects. Far infrared rays emitted by objects of different material compositions vary in wavelength under different ambient temperatures. The wavelength of far infrared rays emitted by human body is usually between 4-20 μm. According to the principles of optics, light waves having the same wavelength can be superimposed. Far infrared rays having the same wavelength as those emitted by the human body are remedial and therapeutic to human body. Far infrared rays having wavelength of 4-20 μm can be easily absorbed by human body and readily be converted into internal energy, stimulating water molecules to vibrate and rub against each other to generate heat energy, resulting in "resonance absorption". When "resonance absorption" occurs, far infrared rays having a wavelength of 4-20 μm can penetrate up to 3-5 cm of human skin, and the water molecules in the targeted cells can generate internal energy through resonance and the internal energy can be absorbed by the human body, thereby accelerating blood circulation, activating cell tissues, promoting metabolism, accelerating nutrient transfer and enzyme activity, excreting harmful substances accumulated in the human body, strengthening the human body's immunity and achieving health benefits. The ceramic footbath boots made of these ceramic materials can release far infrared rays within said range of wavelengths, which exert beneficial health effects on human body. The most ideal ceramic material for making the footbath boots of the present invention is the silicate-based and tourmaline-containing ceramic material as described herein.

3. Applications

Ceramic footbath boots according to the present invention are made of ceramic materials including but not limited to a formula, such as a silicate-based and tourmaline-containing ceramic material. The inner layer of the footbath containers is marked with at least a minimum and a maximum water level lines. In one embodiment, the footbath boots are filled with hot water of above 80° C. until just exceeding the minimum water level mark, and then cold water is gradually added until the water in the cavity of the boots reaches an appropriate temperature for footbath [e.g., 45-50° C.] but the final water level is better not to exceed the maximum water level mark. The top open end of the boots is then covered with the movable canopy. User is better to choose a chair with suitable height and then places his/her left and/or right foot into the ceramic footbath boots. The soles are placed on the exothermic papillary extrusions corresponding to the reflex point zone of the feet, therefore the papillary extrusions can directly stimulate the reflex point zone of the feet, and the papillary shape can provide physical massage to specific contact points and reflex zones of your feet according to the user's needs. The tightness of the boots can be adjusted by fastening the zipper or tightening the drawstring or altering the hook-and-loop fastener of the movable canopy. In addition, the upper part of the boots provides support for the legs and transmits those accumulated heat from the inner layer of the boots directly to the legs such that it helps relax and soothe the user's muscles while enhances the blood flow of the user. The footbath boots of the present invention enable the user to experience exothermic foot massage with flexibility of placing one or both foot in two separate far-infrared containers with a "resonance absorption" radiation space.

4. Effect Comparison (I) Basic Principle

As far infrared ray is a radiant thermal energy, the energy emitter and receiver need to have the same wavelength in order to generate a radiation resonance effect, like the resonance vibration phenomenon generated by rubbing a "fish basin". The materials, which have high emission rate, good insulation capacity and able to emit far infrared rays with the same wavelength as those emitted by human body under an appropriate set of temperatures should be selected. The silicate-based and tourmaline-containing ceramic material has a very high emission rate which can emit far infrared rays with a wavelength of 4-14 μm at an emitting rate of more than 0.92 at room temperature, and has a peak radiation wavelength of 9.1 μm when the surface temperature reaches 45° C. Wavelength of the far infrared ray is very close to those emitted by human body. The principle is very similar to Japan's ceramic bead sand bath that heats up silicate-based ceramic materials to activate the release of far infrared rays.

(II) Effect Of Ceramic Footbath Boots a) Structural Effect: The distance and angle between the user's foot can be readily adjusted according to the user's comfort. The presently disclosed footbath boots are distinct from the traditional designs, as legs can be individually placed in two separate footbath containers for evenly bathing. In addition, the boot-shaped design adaptation of the present invention allows water reaching up to the lower legs. Legs can be placed into two separate far-infrared containers with a "resonance absorption" radiation space at the same time. The upper part of the boot provides support for the legs and transmits those accumulated heat from the inner layer of the boots directly to the legs.

b) Material: The ceramic footbath boots are made of ceramic materials including but not limited to a formula, for example, a silicate-based and tourmaline-containing ceramic material which has a high far infrared emission rate. After directly pouring hot water of above 80° C. into the ceramic footbath boots, the boots can produce and emit far infrared rays with similar wavelength to those emitted by human body in the absence of a power source. Negative ions, weak static current [0.06 mA] that matches the bioelectric current of human body, minerals and trace elements needed by human body are also released from the material. The material is natural, pure, environmental-friendly and pollutant-free. According to the principles of optics, the light waves of the same wavelength can be superimposed. Far infrared rays which have the same wavelength as those emitted by human body are beneficial to and have therapeutic effects on human health. Far infrared rays with a wavelength of 4-20 μm can be easily absorbed by human body and converted into internal energy stimulating water molecules therein to rub against each other and generate heat, resulting in "resonance absorption". Under "resonance absorption", far infrared rays with a wavelength of 4-20 μm can penetrate up to 3-5 cm deep under the human skin, which results in resonance of water molecules to generate internal energy. The internal energy is absorbed by the body, thereby producing various health beneficial effects, such as accelerating blood circulation, activating cell tissues, promoting metabolism, accelerating nutrient transfer and enzyme activity, excreting harmful substances accumulated in the body and strengthening body's immunity. The peak radiation wavelength of the ceramic material containing tourmaline is 9.1 μm when surface temperature reaches 45° C. which produces remedial effects on human body. By pouring hot water of above 80° C. into the ceramic footbath boots can activate far infrared resonance. The ceramic footbath boots neither consume power nor need a power source, so energy is effectively saved, tangling of electrical wires and electrical leakage are avoided.

c) Combinational Effects Of The Material And Structure Of The Present Invention: the inner layer of the footbath containers comprises a plurality of honeycomb-shaped, hexagonal cylinder-shaped or porous network-like lines, and a plurality of papillary extrusions corresponding to reflex point zone of the feet to increase the area of the inner layer in contact with water and to produce more counter electrodes; at the same time, more weak static current [0.06 mA] that matches the bioelectric current of human body is produced which results in electrolytic decomposition when the ceramic material is in contact with water. Water molecules are subsequently broken down into positively charged hydrogen ions and negatively charged hydroxyl group, namely, hydroxyl.

Hydrogen ions immediately combine with the negative electrons emitted by the tourmaline-containing ceramic material to become hydrogen atoms, which are then released into the air, and the remaining hydroxyl ions combine with water molecules to become negatively charged hydroxyl ions, the water in the footbath containers becomes weakly alkaline with a pH value between 7.4-7.6. Meanwhile, under the far infrared radiation, water solubility and penetration are enhanced as the larger molecular groups of water become smaller. Under the following five external conditions, the effects of the tourmaline-containing ceramic materials can be optimally exerted: 1) convection of water and air; 2) increase in temperature; 3) changes in humidity in order to keep the ceramic material in close contact with water to enhance electrolysis and increase the release of negative ions; 4) rubbing; and 5) pressure.

The inner layer of the footbath containers are marked with at least minimum and maximum water level lines. During application, after hot water of above 80° C. is poured into the footbath containers, temperature of the inner layer of the footbath containers rises, and cold water is then gradually added into the containers until the final water temperature reaches an appropriate temperature for footbath [such as 45-50° C.]. However, the water is better not to exceed the maximum water mark. Each boot is covered with a movable canopy and a chair with an appropriate height is selected for stability when the user is sitting on it. The user's feet are placed into the boots of the present invention. The papillary extrusions attached on the inner layer of the boots provide support for the weight of the feet and also increases the surface area for contact with the reflex point zone of the feet. The papillary extrusions also serve as an ideal massaging device because the reflex point zone of the feet can be stimulated and massaged through pressing the reflex point zone on each sole of the feet against the papillary extrusions on the inner layer of each container in order to bring a thermal massage state of mind to the user. The weak static current [0.06 mA] from the ceramic material of the present invention that matches the bioelectric current of human body is also remedial as the current can pass through acupoints on which the foot or leg of the user is in contact with the inner layer of the container. According to user's needs, the papillary extrusions provide on certain acupoints and reflex point zone with an intentional and specific point massage in order to enhance the stimulus to the corresponding acupoints and reflex point zone, and hence improve the initial effect of the ceramic footbath container of the present invention. The meridian acupoints are the best site to receive energy from external environment because effects are multiplied when energy is introduced through these sites. The ceramic footbath containers provide support for legs, and the heat accumulated on the inner layer of the footbath containers can be directly transmitted to the legs, which relaxes and sooths the leg muscles as well as enhances blood flow. Because the tourmaline-containing ceramic material is resistant to acid, alkali and elevated temperatures, hot herbal medicinal formulation can also be directly added into the ceramic footbath containers of the present invention, and the heat from the hot formulation can be preserved in the containers for a longer period of time due to a better heat insulation property in the present invention over the conventional footbath devices. Water or liquid can be easily poured in or out in the absence of a water outlet, and therefore the residual water/liquid can be removed more completely in order to make the footbath containers of the present invention safer and more hygienic. After addition of hot water into the footbath containers, the tourmaline-containing ceramic material of the present invention can emit far infrared rays and bring a warm state of mind to the user from the resonance absorption which is produced by similar far infrared wavelengths of the ceramic material and the human body, and the same state of mind cannot be achieved by using the traditional wooden basins, wooden barrels, plastic basins and similar containers. The present invention has a good thermal insulation capacity and allows the distance and angle between the user's legs be adjusted according to the user's needs.

The present invention overcomes the disadvantages of the conventional footbath containers such as rapid cooling, low water level, inflexibility that require both legs of the user be placed together in one single container, and the heavy reliance on power source and electrical wires. The present invention can produce and emit far infrared rays with similar wavelength to that emitted by human body in the absence of a power source, release negative ions automatically and permanently, produce weak static current [0.06 mA] which matches the bioelectric current of human body, and release minerals and trace elements needed by human body into water. The present invention is energy-efficient, environmental-friendly, economical and durable. Additionally, the present invention is easy to use and clean, and the disposal of which does not pollute the environment.

In view of the foregoing descriptions, the ceramic footbath containers of the present invention are configured to respond to and fit in the five external conditions as defined hereinbefore, as well as for optimal exertion of the silicate-based ceramic materials containing tourmaline on human body. Some advantages of the present invention are summarized as follows: firstly, when hot water is poured into the footbath containers, it makes the temperature of the inner layer of the ceramic footbath boots increase such that the footbath containers emit far infrared rays matching that of human body, and then produce more weak static current [0.06 mA] matching the human's bioelectric currents, leading to a subsequent electrolytic decomposition upon contact with water molecules and produces large amounts of negative ions, minerals and trace elements beneficial to the human body. The hot water, after being electrolyzed, becomes weakly alkaline and is continuously broken down into small molecular groups under the influence of far infrared rays. Through pressing and rubbing against the papillary extrusions corresponding to the reflex point zone of the feet, water turbulence is generated, increasing the generation of the weak static current and the release of negative ions. During pressing and rubbing against the papillary extrusions corresponding to the reflex point zone of feet, the weak static current [0.06 mA] induces remedial effect through the acupoints. The human meridian acupoints are the best site to receive energy from the external environment, providing energy through these specific sites beneficial effects are thereby multiplied. The honeycomb-shaped, hexagonal cylinder-shaped or porous network-like lines of the inner layer of the present invention improves the effect of the papillary extrusions during pressing and rubbing, increases water turbulence and the surface area of the inner layer in contact with water, thereby produces more counter electrodes, more weak static current [0.06 mA] and negative ions. The weak static current [0.06 mA] produced by the ceramic footbath containers matches the bioelectric current of human body, thus triggering the natural bioelectric and biological effects of human bodies, such as promotion of metabolism, regulation of the central nervous system and autonomic nervous system, regulation of the cerebral cortex, and improvement of heart rhythm and blood circulation, especially improvement of microcirculation. It is also a good means for cell membrane and humoral regulation inside and outside the cells, especially for exchange of ions, energy exchange and information exchange. Specifically, the weak static current [0.06 mA] produced by the ceramic footbath containers has three advantages for the human body: 1.) promote cells to arrange in order; 2.) Resist harmful electromagnetic waves; 3.) Benefit the human body through meridian acupoints.

When using the ceramic footbath boots of the present invention, the legs are placed in the far-infrared "resonance absorption" radiation space, and the temperature inside the footbath containers is notably higher than body temperature, resulting in the release of chemical media and vasodilation. Under the thermal effect of far infrared rays, the thermal receptors of skin are stimulated by heat, and the sensory signal passes through afferent sensory fibers to the spinal cord. However, part of the signal is diverted via branches of nerve fibers to the nerve endings dictated to the skin, which results in the release of vasoactive substances and causes vasodilation. This process is known as axon reflex. Thermal stimulation also activates the afferent receptors of skin, and reduces the activity of the adrenergic postganglionic fibers of the vascular smooth muscle, resulting in vasodilation. Vasodilation resulting from local spinal reflex is not confined to the area being heat stimulated, but also in other areas away from it, for example, the thermal effect on legs may accelerate the blood flow under the skin of the head. Considering the thermal effect of far infrared rays and vasodilation resulting from local spinal reflex, vasodilation not only occurs in legs but also in the whole body, thus accelerating the overall blood flow throughout the body. In addition, under the secondary effect of far infrared rays, large and aged molecular groups in body fluids and blood become smaller, and the resistance to blood flow also decreases due to smaller molecular groups; and because the pollutants (such as $CO_2$, $SO_2$ and $Cl_2$) on the surface of water molecular groups are cleared up and blood lipids in blood vessels are reduced, blood viscosity is thus decreased; accelerates blood flow, enhances dilation of capillaries and micro-circulation.

Generally, the body fluids and blood of a healthy individual are weakly alkaline, so nutrient absorption and waste excretion of the cells can normally exert through cell membrane in order to allow metabolism of the cells. However, modern living habits tend to turn the body fluids and blood from weakly alkaline into weakly acidic, rapidly increasing the reactive oxygen species (ROS) (or oxidizing radicals) in the body. The ROS accelerate the oxidation and aging of cells, thicken cell membrane, obstruct transport of substances between cell membrane and affect nutrient absorption and waste excretion, result in weakening of immunity, weakening of cell membrane's ability to protect the cells, and easy invasion by viruses. An important element to determine the pH of body fluids is the concentration of hydrogen ions, the higher the number of hydrogen ions is, the stronger is the acidity of body fluids. A special function of negative ions is to reduce the concentration of hydrogen ions in body fluids. When appropriate concentration of negative ions enter into the body, they can reduce and suppress the number of ROS accumulated in the body, so as to revitalize the cells, purify the blood and restore the normal weak alkalinity. When the weak current carrying negative ions enters into the cells, the cells automatically balance the ion content inside and outside of the cells according to the principle of sodium-potassium adenosine triphosphatase (Na+/K+-ATPase) mechanism, unblock the channels at the cell membrane for nutrient absorption and waste excretion, in order to activate the cell tissues. When negative ions activate the activity of immune cells, the immunity of the recipient is enhanced. Calcium ions are required in breathing, blood circulation, gastrointestinal peristalsis, metabolism and other types of autonomic nerve conduction. If the number of negative ions in the human body increases, the content of calcium ions in the body will increase, making the neural transmission smoother. Simultaneously, the secretion of various enzymes in the human body also increases and the immunity is enhanced. The present invention creates a space for far-infrared "resonance absorption" radiation and emission of weak current and negative ions, which provides a solid platform to achieve these health beneficial outcomes.

Other advantages of the present invention are: the ceramic footbath boots conform to the structure of human body. The foot distance and angle can be adjusted freely for comfort, and acupoints and reflex point zones of the feet can be massaged as desired by the user. Distinct from traditional designs, legs can be placed in separate containers for even heating. In addition, the adaptation of boot-shaped design allows water level to reach to the legs. The boots provide support to the legs and the heat accumulated on the inner layer of the boots can be directly transmitted to the legs for relaxation, soothing leg muscles and enhancing blood flow. Moreover, the concept of ceramic footbath boots can be used for arm bathing and is very good for relieving cervical spondylosis; hot herbal medicinal soup can also be added into the ceramic footbath boots for fumigation of any affected parts or the face, or a few drops of essential oil can be added for facial fumigation, followed by leg spa. Moreover, due to the effect of far infrared rays, negative ions and electrolysis, the ceramic footbath boots have strong antibacterial, antimicrobial, anti-inflammatory, analgesic, detumescent and deodorant functions. They are particularly useful for relieving beriberi (athlete's foot) and foot odor.

In summary, the present invention includes:
(I) Innovative design ideas in overcoming of the shortcomings of existing products: 1. Tailor-made design, which adapts to the structure of human body; 2. separated type, individual legs are placed into separate far-infrared "resonance absorption" spaces; 3. Boot-shaped design, so that water level can reach the shank; 4. The boots add support to the legs, and the heat accumulated on the inner layer of the boots can be directly transmitted to the legs; 5. The papillary extrusions corresponding to the reflex point zone of the feet stimulate the reflex point zone with heat and weak static current [0.06 mA]; 6. During foot bathing, the distance between the foot and the angle of each feet can be adjusted freely for comfort, and acupoints and reflex point zones of that feet can be massaged according to users' needs; 7. A power source is not needed but the present invention uses hot water of above 80° C. as a heat source, triggering the emission of far infrared rays, negative ions, weak static current [0.06 mA], minerals and trace elements needed by human body; 8. The hot water or herbal medicinal soup added into the ceramic footbath boots is not only used for footbath, but also used as a heat source to activate the release of far infrared rays and negative ions, as described hereinbefore; 9. The concept of ceramic footbath boots can apply on arm, and herbal medicinal soup can be added for fumigation of any affected parts or the face, or a few drops of essential oil can be added for facial fumigation, followed by leg spa; 10. Hot water after being electrolyzed becomes weakly alkaline and is broken down into small molecular groups under the influence of far infrared rays, which, in combination with the stimulation of weak static current, improve the heart rate and blood circulation, especially the improvement of microcirculation. It is favourable for cell membrane and humoral regulation inside and outside the cells, especially for the exchange of ions, energy and signals, and also especially for absorption of herbal soup, so as to achieve efficacy faster; 11. Create an environment with high content of negative ions for breathing during facial fumigation; 12. The ceramic footbath boots are highly antibacterial, antimicrobial, anti-inflammatory, analgesic, detumescent and deodorant. They are particularly useful for relieving beriberi (athlete's foot) and foot odor; 13. They improve skin texture, making the skin soft, smooth and elastic;

(II) The present invention provides an novel application of ceramic material and means to fully exploit the physical characteristics thereof: 1. first to use silicate-based and tourmaline-containing ceramic materials to manufacture footbath apparatus; 2. Take full advantage of the high plasticity of ceramic materials; the materials are hard after formation with good thermal insulation performance, and resistance to acid, alkali, corrosion and elevated temperatures; 3. Tourmaline ceramic emit far infrared rays with wavelength of 4-14 microns at an emitting rate of more than 0.92 at room temperature; 4. the release negative ions is both automatic and permanent; 5. Continuously produce weak static current [0.06 mA] that matches the bioelectric current of human body; 6. 11 types of minerals and trace elements are released into water, including magnesium, sodium, iron, manganese, lithium, aluminum, boron, silicon, fluorine, hydrogen and oxygen, among which magnesium, iron, manganese, silicon, fluorine and boron are essential for human bodies or are significant in physiological functions; 7. The tourmaline ceramic materials are natural and non-harmful, and the disposal thereof does not pollute the environment;

(III) The present invention exploits the application of far infrared radiation, circulation, theory of meridians and acupoins and health care theory: 1. The materials emit far infrared rays of the same wavelength as those emitted by human under an appropriate set of temperatures with a high emission rate are selected; 2. Power source and electrical wires are not needed, instead hot water of above 80° C. is used as a heat source to activate the emission of far infrared rays; 3. When "resonance absorption" occurs, far infrared rays with wavelength of 4-20 microns penetrate into human skin up to 3-5 cm deep, so that water molecules in the cells can generate internal energy through resonance and the internal energy can be absorbed by the body, thereby helping accelerate blood circulation, activate cell tissues, promote metabolism, accelerate nutrient transfer and enzyme activity, excrete harmful substances accumulated in the body, strengthen the body's immunity and achieve health beneficial effects; 4. The papillary extrusions corresponding to the reflex point zone of feet stimulate the reflex point zone with heat and weak static current [0.06 mA]; 5. Tourmaline-containing ceramic materials can emit far infrared rays with wavelength of 4-14 microns at an emitting rate of more than 0.92 at room temperature. This is shown to be highly bactericidal, for example, 99.98% for *Candida albicans*, 99.85% for *Staphylococcus aureus*, and over 99% for *Bacillus subtilis*. Furthermore, tourmaline-containing ceramic materials can release negative ions automatically and permanently, where negative ions are antimicrobial, which show significant inhibition against exposed cocci, *Vibrio cholerae, Salmonella typhi* and *Staphylococcus aureus*. Therefore, the present invention has antibacterial, anti-inflammatory, detumescent and deodorant functions;

(IV) The present invention has good thermal insulation, and resistance to acid, alkali, corrosion and elevated temperatures. Hot herbal medicinal soup can be added directly into the ceramic footbath boots, which helps preservation of heat, and the present invention does not deform or release harmful substances when heated or warmed. The ceramic footbath boots do not need a power source and electric wires, thus the risks of electrical leakage and tripping by electric wires are avoided; water injection and drainage can be done conveniently and easy to clean. The ceramic materials of the present invention are natural and non-harmful, and their disposal does not pollute the environment. The present invention is environmentally friendly, energy-efficient, economical, safe and hygienic. The long lasting warm feeling and the close skin contact of the present invention are unachievable by traditional wooden basins, wooden barrels, plastic basins and similar containers. The present invention is a significant advancement in comparison to the existing plastics and rubber footbaths which age, deform and release harmful substances when exposed to heat.

Therefore, the present invention having the foregoing four innovative points provides a simple, practical, revolutionary, economical, environmentally friendly, energy-efficient, safe, hygienic and non-harmful footbath product for consumers, which can also be used as an auxiliary product for physiotherapy.

The invention claimed is:

1. A ceramic footbath apparatus comprises a pair of boot-like footbath containers, wherein said footbath containers are made of ceramic material, and the footbath containers are sintered into double-layered containers having a hollow space between two layers, and wherein an inner layer of the two layers comprises lines with a pattern and attached thereon with a plurality of papillary extrusions corresponding to a reflex point zone of a user's feet, and wherein said pattern of the lines of the inner layer comprises honeycomb-shaped, hexagonal cylinder-shaped or porous network-like for increasing the surface area of the inner layer of the footbath containers in contact with water when water is added into the footbath containers and producing more counter electrodes due to the piezoelectric and thermoelectric properties of the ceramic material, thereby improving the effect of the plurality of papillary extrusions corresponding to the reflex point zone of the user's feet during footbath and massage, enhancing water turbulence to produce more weak static current at 0.06 mA that matches a bioelectric current of a human body, and leading to a release of more negative ions, minerals, trace elements and far infrared rays, and wherein the inner layer is non-glazed for preventing loss of far infrared rays from irradiation while an outer layer of the two layers is glazed for enhancing heat retention and thermal insulation inside the footbath containers.

2. The ceramic footbath apparatus of claim 1, wherein said ceramic material comprises tourmaline-containing silicates.

3. The ceramic footbath apparatus of claim 2, wherein said ceramic material emits far infrared rays with a wavelength of 4-14 µm at an emission rate of more than 0.92 at room temperature.

4. The ceramic footbath apparatus of claim 1, wherein said plurality of papillary extrusions corresponding to the reflex point zone of the user's feet is capable of pressing and/or massaging the feet on a specific reflex point zone according to the user's needs which corresponds to the affected parts of the user, and providing a stimulation through the papillary extrusions being heated by hot water added to the boot-like footbath containers, and wherein the piezoelectric and thermoelectric properties of the ceramic material under the elevated temperature in the hot water and pressure applied by the feet of the user provides the material for producing the weak static current at 0.06 mA that matches the bioelectric current of the human body and said weak static current exerts biological effects and stimulation of the bioelectric current on the human body via human acupoints and based on a sodium-potassium pump mechanism.

5. The ceramic footbath apparatus of claim 1, wherein said footbath containers are configured to provide a far-infrared resonance absorption radiation space and an emitting space for weak current and negative ions to facilitate the bioelectric effects based on a sodium-potassium adenosine triphosphatase mechanism on cell activation, vasodilation, size reduction of water molecules of body fluids and blood, reduction in blood lipid level, restoration of blood pH level to a weakly alkaline level, improvement in microcirculation, promotion of metabolism, purification of blood, strengthening of immune system and modulation of autonomic nervous system.

6. The ceramic footbath apparatus of claim 1, wherein a top open end of each of said footbath containers is relatively more elevated at a front portion than a rear portion, and the relatively more elevated front portion forms an arch shape while the rear portion is relatively lower than the front portion and has a U-shaped notch.

7. The ceramic footbath apparatus of claim 1 further comprises a movable canopy sewn with thermal insulating fiber, wherein the canopy comprises a zipper, drawstring or hook-and-loop fastener for tightness adjustment at a top open end of each of said footbath containers.

8. The ceramic footbath apparatus of claim 1, wherein the inner layer of said footbath containers are marked with at least a minimum and a maximum water level lines.

9. A method for manufacturing a footbath apparatus comprising using a ceramic material to form a pair of boot-like footbath containers with an inner layer, an outer layer, and a hollow space between two layers, providing lines with a pattern on said inner layer and attached thereon with a plurality of papillary extrusions corresponding to a reflex point zone of a user's feet, sintering the footbath containers, and glazing the outer layer while the inner layer is non-glazed, wherein said footbath containers after being added with hot water emit far infrared rays with a similar wavelength to those emitted by a human body and generate a far-infrared resonance absorption radiation space, and wherein said ceramic material emits far infrared rays with a wavelength of 4-14 µm and at an emission rate of more than 0.92 at room temperature.

10. The method of claim 9, wherein said ceramic material comprises tourmaline-containing silicates.

11. The method of claim 9, wherein said ceramic material is capable of automatically and permanently releasing negative ions, continuously producing weak static current at 0.06 mA that matches a bioelectric current of the human body, and releasing mineral matters and trace elements needed by the human body into the surrounding water.

* * * * *